US008649526B2

(12) United States Patent
Vernon

(10) Patent No.: US 8,649,526 B2

(45) Date of Patent: Feb. 11, 2014

(54) NOISE REDUCTION CIRCUIT AND METHOD THEREFOR

(75) Inventor: Scott Dennis Vernon, Chandler, AZ (US)

(73) Assignee: NXP B.V., Eindhoven (NL)

(*) Notice: Subject to any disclaimer, the term of this patent is extended or adjusted under 35 U.S.C. 154(b) by 403 days.

(21) Appl. No.: 12/875,871

(22) Filed: Sep. 3, 2010

(65) Prior Publication Data

US 2012/0057718 A1 Mar. 8, 2012

(51) Int. Cl.
*A61F 11/06* (2006.01)

(52) U.S. Cl.
USPC .......................................... 381/71.6; 381/71.1

(58) Field of Classification Search
USPC .......... 381/71.1, 71.6, 71.9, 71.12, 73.1, 94.1
See application file for complete search history.

(56) References Cited

U.S. PATENT DOCUMENTS

| | | | | |
|---|---|---|---|---|
| 703,188 | A * | 6/1902 | Jones | 235/3 |
| 6,134,329 | A * | 10/2000 | Gao et al. | 381/60 |
| 7,103,188 | B1 * | 9/2006 | Jones | 381/71.9 |
| 7,715,577 | B2 * | 5/2010 | Allen et al. | 381/312 |
| 8,229,127 | B2 * | 7/2012 | Jorgensen et al. | 381/71.6 |
| 2003/0185403 | A1 | 10/2003 | Sibbald | |
| 2009/0080670 | A1 * | 3/2009 | Solbeck et al. | 381/71.6 |
| 2010/0105447 | A1 * | 4/2010 | Sibbald et al. | 455/570 |
| 2010/0246847 | A1 * | 9/2010 | Johnson et al. | 381/74 |

FOREIGN PATENT DOCUMENTS

WO WO-2008138349 11/2008

* cited by examiner

*Primary Examiner* — Vivian Chin
*Assistant Examiner* — Ammar Hamid

(57) ABSTRACT

Noise cancellation is effected for audio devices. In connection with various embodiments, a forward leakage transfer function is determined using a signal corresponding to detected portions of the generated sound that has leaked out of the user's ear canal with the proximate end of the earphone inserted in (or otherwise fitted to) the ear. This forward leakage transfer function can be used to characterize ambient noise entering a user's ear canal. A signal corresponding to ambient noise is processed with the forward leakage transfer function to generate and output a noise-cancelling signal for canceling at least a portion of the detected ambient noise.

21 Claims, 4 Drawing Sheets

NOISE REDUCTION CIRCUIT AND METHOD THEREFOR

Aspects of various embodiments of the present invention are directed to noise reduction, and particular aspects are directed to noise reduction with audio devices for fitment with a user's ear.

Audio speakers have been used in various forms for many years, for enjoying music or movies, listening to broadcast programs, instructional use and communications. Audio speakers have taken many forms, ranging from loudspeakers for the use of many, to personal speakers used in headsets, earphones and earbuds.

For personal listening enjoyment, the presence of ambient noise can be quite undesirable. For example, users listening to speakers in headphones, earphones or earbuds may experience undesirable ambient noise, relative to sound generated by the speakers. This issue becomes particularly challenging to overcome when a user wishes to listen at relatively low volume levels, at which ambient noise can be heard over sound coming from the speakers.

While many attempts have been made to address noise using active noise reduction, such as those involving feedback systems, feedforward systems, and adaptive systems, these approaches have been limited for many applications. For instance, a leaky earbud-type headphone speaker can exhibit different noise leakage into the ear canal as the earbud shifts in position.

These and other matters have presented challenges to noise cancellation and related devices.

Various example embodiments are directed to noise cancellation for audio devices, such as headsets, earphones and earbuds.

In accordance with an example embodiment, an earphone device includes a housing, a speaker, a microphone and a noise reduction circuit. The housing has a proximate end configured for fitment to a user's ear, and a distal end located opposite the proximate end and configured for placement near an outer portion of the user's ear (e.g., the housing extends from the proximate end, near the user's ear canal, to the distal end away from the user's ear canal). The speaker is configured to generate sound based upon an audio signal for passing into the user's ear canal via the proximate end of the housing. The microphone is located at the distal end and configured to detect ambient noise as well as portions of the generated sound leaked from inside the user's ear canal, with the proximate end of the housing inserted into a portion of the user's ear (e.g., to detect sound leaked past and/or through the housing). The noise reduction circuit generates a forward leakage transfer function for estimating noise entering the user's ear canal, based upon the detected leaked portions of the generated sound, and processes a signal corresponding to the detected ambient noise with the forward leakage transfer function to generate a noise-cancellation signal. This noise-cancellation signal is output for use with the audio signal to generate sound to cancel at least a portion of the ambient noise that passes into the user's ear canal.

Another example embodiment is directed to an audio noise reduction circuit for reducing ambient noise audible to a user listening to sound generated by an earphone device having a proximate end inserted into the user's ear, a speaker for generating sound in response to an audio signal, and a microphone at a distal end of the earphone device for positioning outside of the user's ear canal. The audio noise reduction circuit includes an evaluation circuit that determines a forward leakage transfer function for characterizing ambient noise entering the user's ear canal, using a signal corresponding to portions of the generated sound (as detected by the microphone) that has leaked out of the user's ear canal with the earphone device inserted in the ear. The audio noise reduction circuit also includes a noise reduction circuit that processes a signal corresponding to ambient noise, detected by the microphone, with the forward leakage transfer function to generate and output a noise-cancelling signal for canceling at least a portion of the detected ambient noise.

In connection with another example embodiment, ambient noise audible to a user listening to sound generated by an earphone device is reduced as follows. The earphone device generally has a proximate end inserted into a user's ear, a speaker for generating sound in response to an audio signal, and a microphone at a distal end of the earphone device for positioning outside of the user's ear canal. In an evaluation circuit, a forward leakage transfer function is determined for characterizing ambient noise entering the user's ear canal, using a signal corresponding to portions of the generated sound (as detected by the microphone) that has leaked out of the user's ear canal while the proximate end of the earphone is inserted in the ear. In a noise reduction circuit, a signal corresponding to ambient noise (detected by the microphone) is processed with the forward leakage transfer function to generate and output a noise-cancelling signal for canceling at least a portion of the detected ambient noise.

The above discussion/summary is not intended to describe each embodiment or every implementation of the present disclosure. The figures and detailed description that follow also exemplify various embodiments.

Various example embodiments may be more completely understood in consideration of the following detailed description in connection with the accompanying drawings, in which.

Figure 1A:
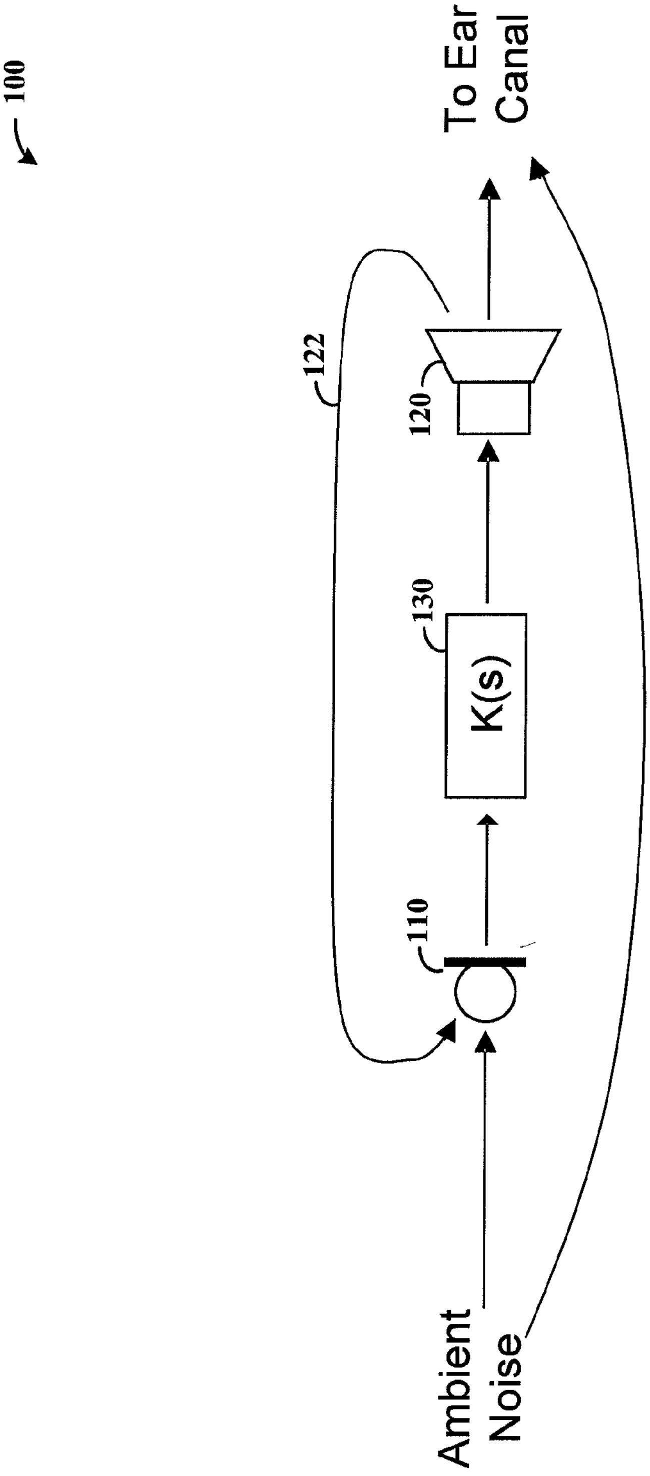
FIG. 1A shows a noise reduction circuit, in accordance with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

Aspects of present invention are believed to be applicable to a variety of different types of processes, devices and arrangements for use with audio speakers such as headsets, earphones, earbuds and other speaker devices having a portion thereof for fitment to a user's ear. While the present invention is not necessarily so limited, various aspects of the invention may be appreciated through a discussion of examples using this context.

According to an example embodiment, noise cancellation is effected using a forward transfer function that represents the propagation of sound into a user's ear canal, together with detected ambient noise, to generate an inverted noise-cancellation signal. The inverted noise signal is presented into the user's ear canal (e.g., by adding the inverted noise signal to an audio or white noise signal for cancelling some or all of the ambient noise).

In various embodiments, noise-cancellation approaches as discussed herein can be used to generate a tailored forward transfer function that is specific to particular applications, including aspects of a specific user's ear and other characteristics of the presentation of audio sound to the user. Accordingly, various embodiments are also directed to such noise cancellation approaches involving the determination of a forward transfer function, with an earbud or earphone device that may not tightly seal to a user's ear, and that further fits differently to different user's ears based upon the geometry of the ear.

In connection with a more particular example embodiment, a forward transfer function is estimated or otherwise determined using a microphone located near an outer portion of and/or outside of a user's ear canal. Leaked sound from the ear canal is detected using the microphone and processed (e.g., in a processing circuit) to determine the forward transfer function. This determined function is then used with detected ambient noise to develop an inverted noise-cancellation signal, which is output for use in cancelling noise, such as by adding the signal to an audio signal used to generate sound for the user and to cancel at least a portion of noise entering the user's ear canal. For instance, an inverted signal corresponding to detected ambient noise can be multiplied by the forward leakage transfer function, to generate the noise-cancellation signal.

In another example embodiment, a forward transfer function for sound passing into a user's ear canal is determined and used to effect noise cancellation as follows. Sound is generated with a speaker device inserted into a user's ear (e.g., in an interconchal region near the ear canal), and portions of the generated sound that are leaked from the user's ear canal are detected. This detected leaked sound is used, together with a known audio signal from which the sound is generated, to determine the forward transfer function. The determined forward transfer function is used with detected ambient noise to develop an inverted noise-cancellation signal, which is added to the audio signal to generate sound for the user. This generated sound has characteristics of the audio signal as well as ambient noise-cancellation sound.

The forward transfer function can be determined using a variety of inputs, processing approaches and circuits. In some implementations, detected leaked sound is used together with a known audio signal as discussed above to determine a reverse leakage transfer function that characterizes the leakage of sound from the user's ear canal while the user is listening to audio. The reverse leakage transfer function may, for example, be used to characterize audio sound leaked by an earphone or earbud that is inserted into the user's ear. The forward transfer function is then estimated (e.g., determined) based upon this reverse leakage transfer function, which is also specific to the user's ear canal and the speaker device used to generate the audio sound.

In various embodiments, the forward leakage transfer function is also determined using other characteristics of the environment. For instance, a user may set an input parameter such as a parameter pertaining to an environmental condition, earbud size, gain or level of noise cancellation, speaker device use (e.g., inside a helmet, in open air, underwater), and others. These user inputs are used together with detected leaked noise to determine the forward leakage transfer function.

In other example embodiments, a dynamic approach is used to determine a forward leakage transfer function for characterizing sound entering a user's ear canal. The forward leakage transfer function is dynamically generated to adaptively cancel noise based upon changing characteristics of the forward leakage function, such as those relating to the positioning of an earphone housing in a user's ear. Inverted signals corresponding to noise are processed as varying ambient noise is detected, using the dynamically generated forward leakage transfer function. This approach can be implemented with one or more of the above embodiments, or others as discussed herein, and can accommodate for changing ambient conditions. For example, many speaker devices are configured for insertion into a user's ear, the speaker device may shift or otherwise move during use. Other environmental conditions, such as heat, pressure, the presence of fluid (e.g., perspiration, water) and others may also affect the manner in which sound propagates into a user's ear canal. Accordingly, the forward leakage transfer function may change dynamically. With this approach, noise cancellation is adjusted dynamically to address environmental changes.

Dynamic active noise cancellation is effected under a variety of conditions. For example, when a user is listening to an audio source, such as music, a radio broadcast, a television broadcast or dialogue, a forward leakage transfer function can be estimated as discussed above using the audio that the user is listening to as an input and also for determining leaked sound. When the audio that the user is listening to is interrupted, such as when the audio pauses or stops (e.g., in the absence of a sample audio signal present for estimating leakage), noise cancellation may pause, stop, or continue using a last-known leakage condition for estimating a forward leakage transfer function (e.g., use a previously-generated forward leakage transfer function). For example, when a user is listening to music, sound is often not generated between songs. During these periods, noise cancellation can be carried out using a previously-generated or last-known forward transfer function as estimated using a song that has just ended, until a next song begins. When an audio signal resumes, the resumed audio signal can then be used to generate a new forward leakage transfer function as discussed herein, for generating a new noise-cancellation signal.

In connection with other example embodiments, a sample audio source is used for estimating a forward leakage transfer function for cancelling noise entering a user's ear canal. The sample source may, for example, be a test signal that is applied to a speaker to generate and present audio sound to a user's ear canal, and leaked portions of the generated sound are detected and used to estimate the forward leakage transfer function. The test signal may, for example, be used to generate audible sound or to generate sound that is substantially inaudible to a user, such as ultrasound, infrasound or sound near the limits of human detection (e.g., near 20 Hz or near 20 kHz).

Generating inaudible sound may, for example, be used in a silent mode of operation, to effect noise cancellation in the absence of any audio signal that can be used for determining a forward leakage transfer function. By generating inaudible sound and detecting leakage of the inaudible sound, a forward transfer function can be estimated or dynamically estimated and used to cancel noise without necessarily presenting audio to the user.

In some embodiments, generating audible sound includes generating white noise, the leakage of which out of a user's ear can be detected. As with the inaudible example above, a forward transfer function is estimated based upon leaked white noise, and used to generate a noise-cancelling signal corresponding to detected ambient noise.

Other embodiments are directed to generating a noise-cancelling signal for filtering out only certain aspects of ambient sound/noise. For example, when a user wishes to hear spoken words yet filter out other ambient noise such as machine noise or engine noise, a noise-cancelling signal can be generated as discussed above using a forward transfer function and specifically avoiding the cancellation of sound being desirably heard. Such an approach may involve applying the forward transfer function to detected ambient noise in a certain frequency range that corresponds to the noise to be filtered out, while avoiding other ranges such as the voice frequency range (e.g., 300-3400 Hz). Other embodiments involve further enhancing or amplifying detected ambient sound that is desirably heard, such as sound in the voice frequency range, to assist passage into the user's ear canal as may otherwise be hindered by an earbud or earphone component.

As may be implemented in connection with embodiments as described herein, an approach to filtering out certain aspects of ambient sound/noise involves sampling undesirable background noise, and using the sample to generate a noise-cancelling signal. For example, a noise-cancelling circuit can be placed in a "sample" or configuration mode and used to sample undesirable noise during a sample period, to determine characteristics of the undesirable noise such as frequency-related characteristics, for filtering selected ambient background noise. A microphone is used to detect frequency characteristics of the ambient noise to be filtered, and a noise reduction circuit processes a signal corresponding to the detected ambient noise. For instance, a forward leakage transfer function can be used to process a signal corresponding to ambient noise in the frequency range of the background noise detected by the microphone. With this approach, noise in the selected frequency range can be reduced while facilitating the audibility of ambient sound in other frequency ranges. For example, when other sound is present with ambient background noise, such as may be generated from music or by a person speaking, some or all of the background noise is canceled while other ambient sound is not. One such approach involves allowing background noise in the voice frequency range (e.g., 300-3000 Hz) to pass, while other ambient noise is filtered. This approach enables the cancelling of undesirable background noise while permitting a user to hear desirable ambient sound.

In connection with another example embodiment, a noise-cancelling circuit is configured to generate a forward leakage transfer function that represents an (estimated) amount of ambient noise that enters a user's ear canal. The noise-cancelling circuit is further configured to use the forward leakage transfer function with an audio signal representing ambient noise to generate an inverted signal for cancelling ambient noise entering the user's ear canal. The noise-cancelling signal effectively uses the forward leakage transfer function to estimate an amount of detected ambient noise that will reach a user's eardrum, and generates a signal corresponding to an inversion of the estimated amount to cancel that noise in the user's ear canal.

Other example embodiments are directed to audio devices such as speakers, headsets, earphones or earbuds, including a speaker for generating sound from an audio signal, a microphone for detecting ambient noise, and noise-cancellation circuitry that generates a noise-cancelling signal for presentation to the speaker, using approaches such as those discussed above. The speaker, microphone and noise-cancellation circuitry are placed in such a manner to facilitate fitment of the audio device for personal use, with the microphone placed near an outer portion of, or outside of, the user's ear canal.

In one embodiment, an earphone or earbud type of audio device includes an end portion configured for insertion into a user's ear, with an opposite end portion including a microphone outside of, or near an outer portion of, the ear canal. The noise-cancellation circuitry dynamically samples audio leakage from the user's ear canal and uses the sampled leakage to adaptively modify the forward transfer function and accordingly adapt the generation of noise-cancellation sound to estimated forward leakage due to the positioning of the earphone or earbud.

In some implementations, the earphone includes a single microphone placed outside the ear canal for sensing audio (e.g., music) leakage from inside the user's ear, past the earphone or earbud including a speaker. The noise-cancellation circuitry uses this information to determine a reverse audio leakage transfer function for audio escaping the user's ear canal, which is in turn used to estimate a forward leakage transfer function for the noise entering the user's ear canal. The single microphone also detects ambient noise, which the noise-cancellation circuitry inverts and processes with (e.g., multiplies by) the forward leakage transfer function to generate a noise-cancellation audio signal. The earphone adds this resulting signal to a source signal (e.g., music) sent to the speaker, thus reducing the noise in the ear without necessarily placing a microphone in the user's ear canal.

In a more particular example embodiment, a single microphone as discussed above is used as follows. A portion of a microphone signal (for detected sound) that corresponds to a speaker input signal is extracted, referred to in the following as mic_sp. The portion of the earbud microphone signal that does not correspond to the speaker input is the noise signal, and referred to in the following as mic_n. An adaptive routine is executed to map the speaker input signal to mic_sp, and the output of this routine is f(s). The routine is adaptable in the sense that it works for various earbud position recordings. Another routine uses f(s) to produce an approximation to 1/f(s), and another routine adds the speaker input signal a noise cancelling component represented by the following equation:

$$(-1*mic\_n)/f(s) \qquad \text{Equation A}$$

The resulting signal, which includes the speaker input signal and added noise cancelling component in Equation A, is presented to a speaker for generating sound corresponding to the speaker input signal and cancelling sound, the latter of which is used to cancel at least some of the ambient noise that enters the user's ear canal.

In connection with various embodiments as discussed herein, terms such as earphone, earbud, headphone, headset and others relating to audio speaker devices for which noise cancellation is effected may be used interchangeably. For example, terms such as earphones, earbuds and headphones are often used interchangeably by different sources to apply to relatively similar devices. In this context, embodiments described herein and shown in the figures may be applicable for implementation with various devices that may be different with that shown (e.g., in FIG. 1B) or described.

Similarly, terms referring to the fitment or insertion of an earphone, earbud or other audio device into a user's ear generally refer to insertion into a portion of a user's ear near the user's ear canal, for directing sound into the user's ear canal. Accordingly, various embodiments involve the fitment or insertion of an audio device into or otherwise near a portion of the user's ear leading into the ear canal.

Turning now to the Figures, FIG. 1A shows a noise reduction circuit 100, in accordance with another example embodiment of the present invention. The noise reduction circuit 100 includes a microphone 110, a speaker 120 and an audio signal processing circuit 130 that generates a noise-cancelling signal. The speaker 120 is configured for generating sound corresponding to an audio signal and providing the sound to a user, such as via an earphone or earbud type of device. The microphone 110 detects audio that is generated by the speaker 120 and leaked or reflected from within the user's ear canal. The microphone also detects ambient noise, and provides a signal corresponding to ambient noise and the leaked audio to the audio signal processing circuit 130.

The audio signal processing circuit 130 uses the leaked audio, as detected by the microphone 110, to determine a forward leakage transfer function for noise entering the user's ear canal. This forward leakage transfer function represents a characterization of noise entering the user's ear canal, as affected by an earphone or earbud device as worn by the user and effectively blocking some of the ambient noise from entering the ear canal. This forward leakage transfer function thus permits an estimation of an amount of ambient noise that is actually audible to the user.

Using this forward leakage transfer function and a signal corresponding to ambient noise as detected by the microphone 110, the audio signal processing circuit 130 generates a noise cancelling signal and presents the noise cancelling signal to the speaker 120, which responds by generating sound to cancel ambient noise entering the user's ear canal. The noise cancelling signal may, for example, be added to an audio signal presented to the speaker 120 for playback, or be added to an audio signal that is presented to an audio processing circuit that, in turn, generates an output for operating the speaker. In this context, the resulting sound generated by the speaker 120 includes noise-canceling sound, thus reducing the amount of noise audible to the user and enhancing the user's ability to listen to the audio signal as provided by a particular source (e.g., by a music player or broadcast device such as a radio or television).

This forward leakage transfer function may be generated in a manner consistent with one or more embodiments as discussed above, such as by developing the inverse of a reverse leakage transfer function determined via the leaked sound detected at the microphone 110. In such an approach, the audio signal processing circuit 130 first generates a reverse leakage transfer function based upon the detected leaked noise as determined via the microphone 110, then estimates the forward leakage transfer function from the reverse leakage transfer function, as an inverse and/or considering other modifications (e.g., where simply inverting the reverse leakage transfer function is inaccurate). This determination of a forward leakage transfer function can thus be based upon a variety of factors, including those discussed herein.

Audio detected at the microphone 110 is processed for determining portions of the audio that correspond to sound and to ambient noise, using one or more approaches. In one embodiment, the audio signal processing circuit 130 uses an input audio signal, such as that corresponding to music (with noise-cancellation added if appropriate), provided to the speaker 120 to separate or otherwise identify leaked sound from the user's ear canal as relative to ambient noise. For example, using the known audio signal provided to the speaker, a portion of the combined noise/reverse leakage sound detected can be separated, with the remaining detected sound corresponding predominantly to ambient noise.

Figure 1B:
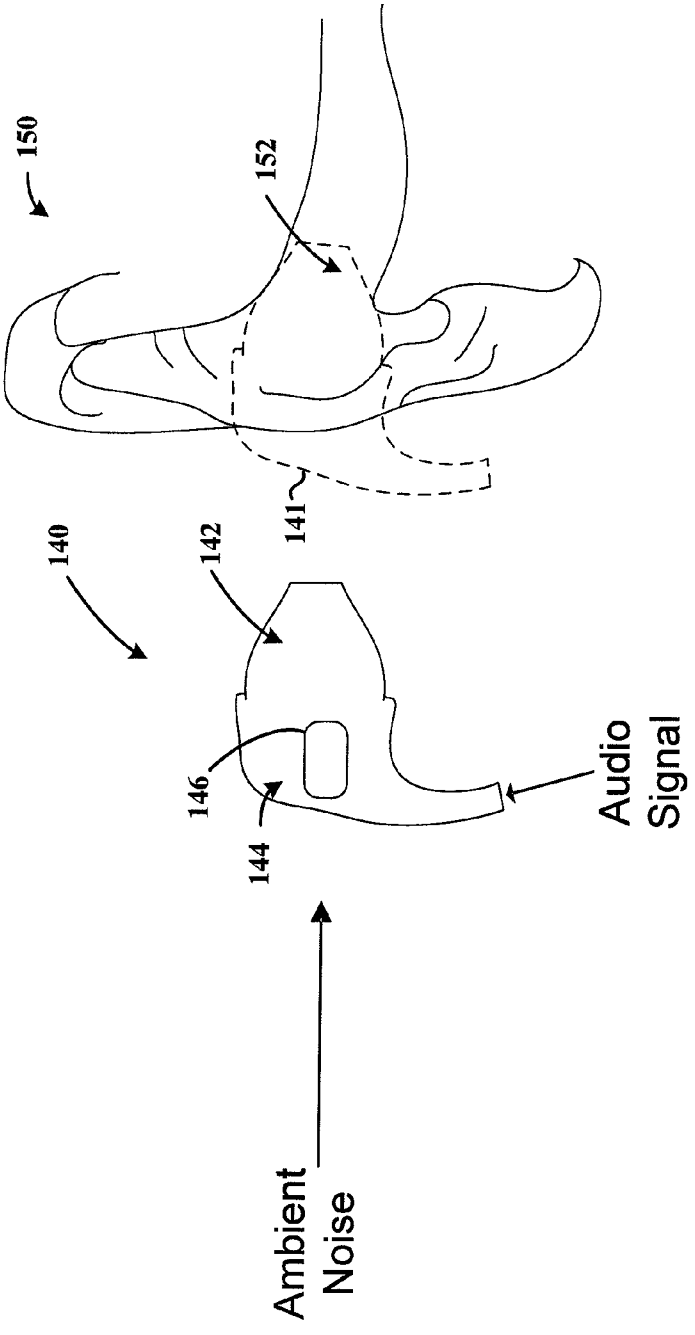
FIG. 1B shows an earbud type of arrangement, in accordance with another example embodiment of the present invention.

FIG. 1B shows an earbud type of device 140 that includes noise cancellation circuitry within an earbud housing, in accordance with another example embodiment of the present invention. The earbud device 140 is configured for fitment with a user's ear 150, having a proximate end 142 for insertion into the user's ear near the ear canal 152 (e.g., as shown by dashed device 141). A distal end 144 of the earbud device 140 remains outside the user's ear canal 152 near an outer portion of the ear 150, and noise-cancelling circuitry 146 is located within the earbud. The earbud device 140 includes a speaker positioned for providing audio sound into the user's ear canal 152 via the proximate end 142, such as at a location between the proximate end 142 and distal end 144. The earbud device 140 also includes a microphone near the distal end 144, which is configured to detect ambient noise and audio generated by the earbud device and leaked out of the user's ear canal 152, past the proximate end 142 of the earbud device.

The noise-cancelling circuitry 146 is configured to operate in accordance with one or more embodiments as discussed herein. Specifically, the noise-cancelling circuitry 146 uses leaked audio detected via the microphone of the earbud 140 to determine a forward leakage transfer function. The noise-cancelling circuitry 146 further uses the leakage transfer function and ambient noise detected via the microphone to generate a noise-cancelling signal that is presented to the earbud's speaker, which generates audio sound based upon an incoming audio signal as shown, as well as noise-cancelling sound.

As discussed above, the noise reduction circuit 100 in FIG. 1A can be used with a variety of devices. In this context, a single design for a noise reduction circuit can be implemented with many different types of headphones, earphones, earbuds and related equipment, without necessarily tailoring the noise cancellation to the specific device as the adaptive nature of the noise cancellation is specific to the leaked sound for the particular application. For instance, as applicable to FIG. 1B, the noise reduction circuit 110 can be integrated with the circuitry 146 in the earbud 140. For example, the speaker 120 can be located near the proximate end 142 of the earbud, or at a transition between a soft portion of the proximate end (for insertion and fitment into the ear 150, near the ear canal 152), and a distal portion 144. The microphone 110 can be located at the distal end 144 of the earbud 140, for detecting ambient noise and leaked audio from the ear canal 152. The noise-cancelling circuitry 130 can further be implemented as the circuitry 146 shown in FIG. 1B.

Figure 2:
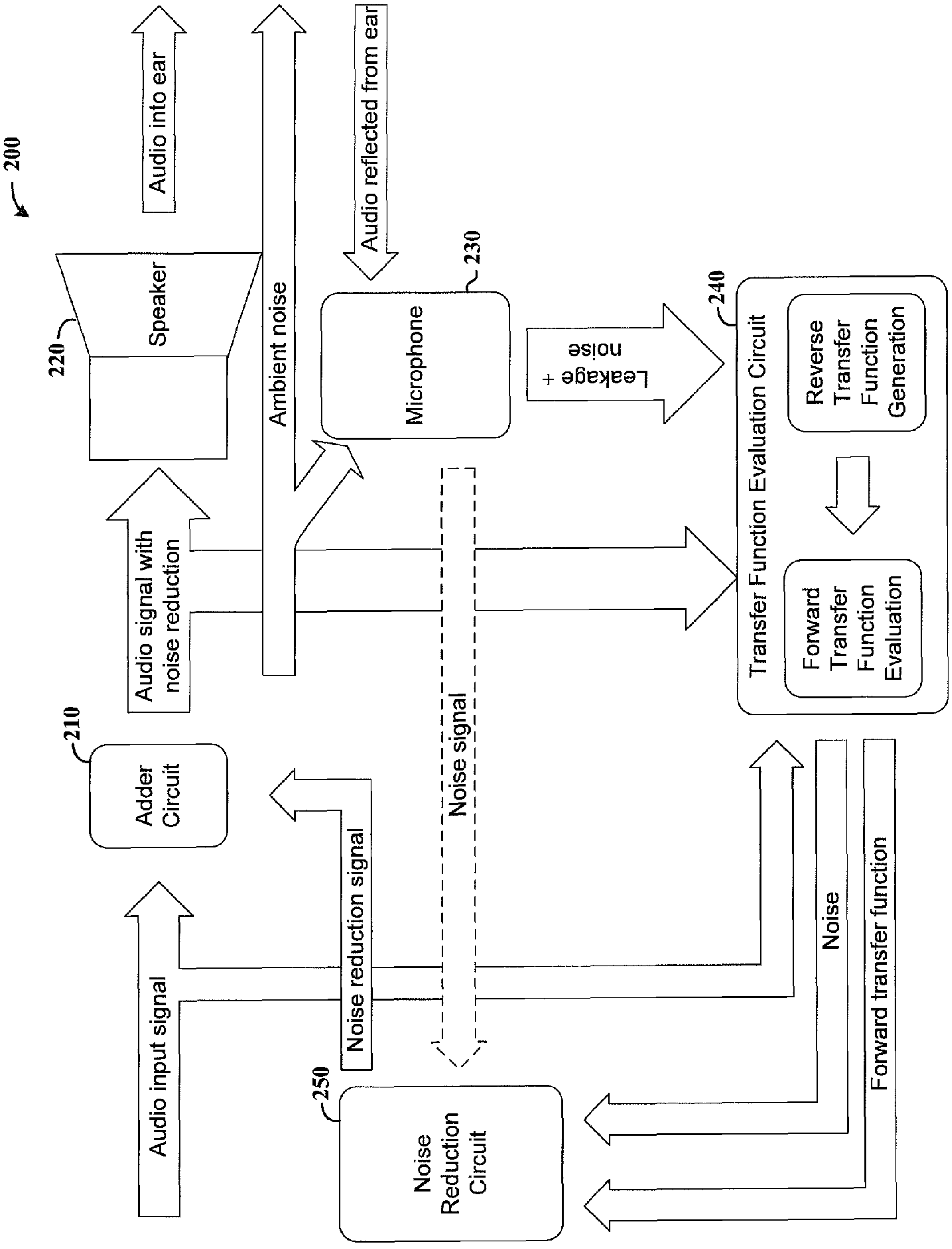
FIG. 2 shows a block diagram for an audio headphone circuit, in accordance with another example embodiment of the present invention.

FIG. 2 shows a block diagram for an audio headphone circuit 200, in accordance with another example embodiment of the present invention. The audio headphone circuit 200 includes an adder circuit 210, speaker 220, microphone 230, transfer function evaluation circuit 240 and a noise reduction circuit 250, some or all of which may be integrated with one another (e.g., as part of a common noise reduction circuit). The audio headphone circuit 200 may, for example, be implemented with an earbud type of arrangement such as that shown in FIG. 1B or otherwise described herein, using the speaker 220 to present audio into a user's ear canal.

The audio headphone circuit 200 receives an audio source signal from an audio source as described herein, and processes the audio signal with an adder circuit 210 that adds a noise reduction signal component (discussed later) to the audio source signal to present a modified audio signal with noise reduction to the speaker 220. The speaker uses this signal to generate sound that is presented into a user's ear.

The microphone 230 detects ambient noise, some of which is also passed into the user's ear, and also detects audio leaking from the user's ear canal. This leaked audio includes audio corresponding to the audio input signal as received at the adder circuit 210, and is presented to the transfer function evaluation circuit 240. The detected leaked audio is presented to the transfer function evaluation circuit 240, used together with the audio signal presented to the speaker 220 (either directly via the audio input signal or the modified audio signal with noise reduction), to generate a reverse transfer function. Where a combined noise/leaked audio signal is presented together, the transfer function evaluation circuit 240 uses the audio signal presented to the speaker 220 to identify a component of the combined noise/leaked audio, as detected at the microphone 230, that corresponds to the leaked audio (e.g., by disregarding and/or separating a noise component for later use). This reverse transfer function is then used to evaluate (e.g., estimate) a forward transfer function, also in the transfer function evaluation circuit 240.

The noise reduction circuit 250 uses the forward transfer function, together with a noise signal detected by the microphone 230, to generate and present a noise reduction signal to the adder circuit 210. The noise signal may be obtained, for example, by determining an ambient noise component of sound detected at the microphone 230 and using that component with the forward leakage transfer function to generate an inverted signal corresponding to an expected amount of noise leaked into the user's ear canal. The noise signal may be obtained via the transfer function evaluation circuit 240, as part of the circuit's determination of the leaked audio component using the audio signal presented to the speaker 220. For example, sound detected at the microphone and corresponding to the audio signal can be identified as leaked audio, whereas the rest of the signal can be detected as noise. Accordingly, the noise signal as shown in FIG. 2 may be provided to the noise reduction circuit 250 via the transfer function evaluation circuit 240, or directly from the microphone 230.

Figure 3:
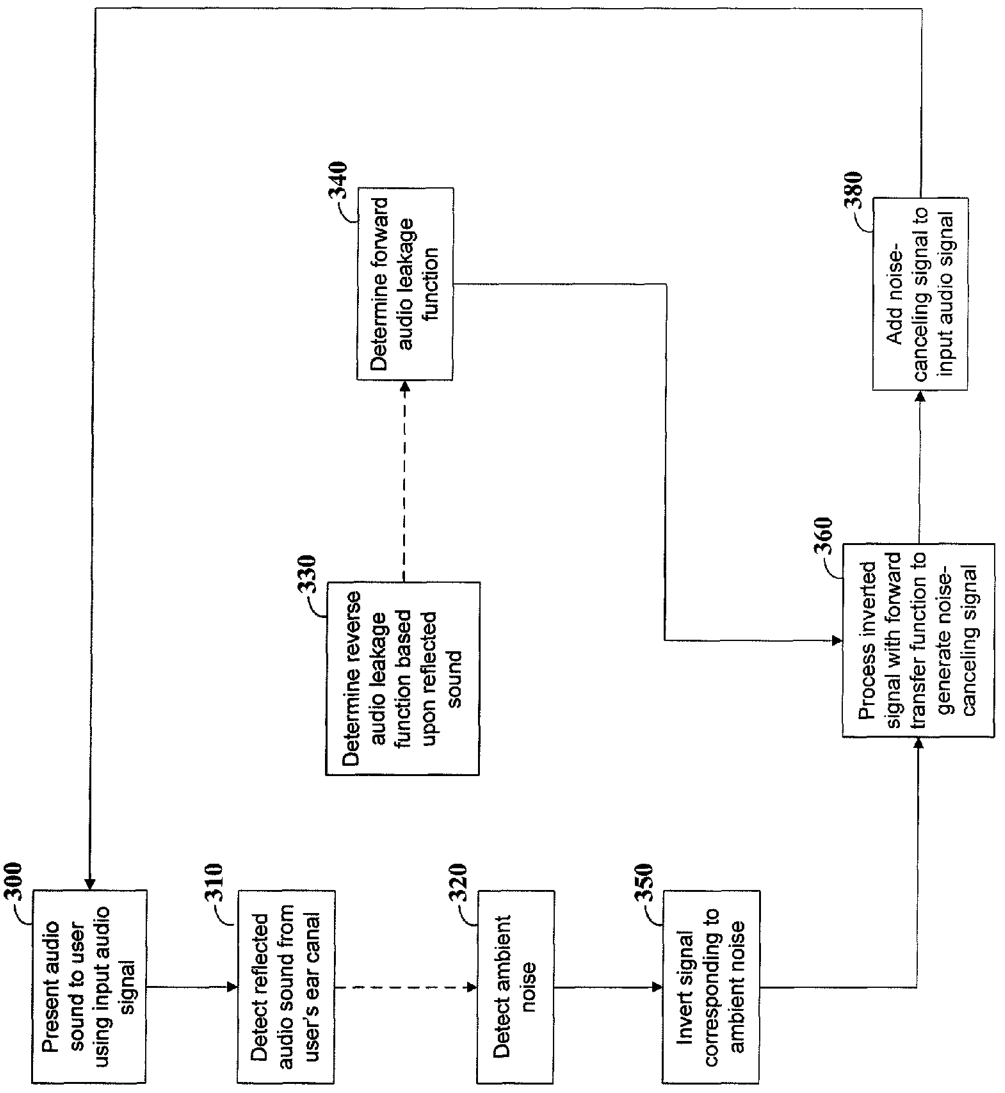
FIG. 3 shows a flow diagram for cancelling noise, according to another example embodiment of the present invention.

FIG. 3 shows a flow diagram for cancelling noise, according to another example embodiment of the present invention. At block 300, audio sound is presented to a user via the user's ear canal, based upon an input audio signal from an audio source such as a music player, broadcast receiver (e.g., radio or television), mobile telephone or white noise generator. The sound may be presented using headphones, earphones or an earbud such as that shown in FIG. 1B.

At block 310, reflected or leaked audio sound from the user's ear canal is detected using a microphone, which can be located at an outer portion of the ear canal. At block 320, ambient noise is also detected using the microphone. These detection steps can be carried out simultaneously, with the respective noise and leaked audio signals separated or otherwise differentiated as appropriate for processing in order to identify portions of detected sound respectively corresponding to noise and leaked audio. In certain embodiments, the noise signal is not separated from detected sound, with either the combined signal being used or a portion of the overall signal corresponding to leaked audio being used based upon a known input audio signal.

The following steps involving the determining of a forward leakage transfer function may be carried out in a different sequence, relative to ambient noise processing steps discussed later. Certain steps may further be combined. In one implementation, block 330 is not used and a forward audio leakage transfer function is determined at block 340, using the reflected audio sound detected at block 310. In another implementation, blocks 310 and 330 are not used, with the forward leakage transfer function being generated at block 340 independently of such steps.

When used, block 330 involves determining a reverse audio leakage transfer function based upon reflected or leaked sound from the use's ear canal. The reverse audio leakage transfer function is then used at block 340 to determine a forward audio leakage transfer function to characterize leakage (passage) of ambient noise into the user's ear canal, past an earphone, earbud or headset type of device worn by the user. Accordingly, the leakage of a known audio sound as presented at block 300 out of a user's ear canal can be used to estimate leakage of ambient noise into the user's ear canal.

At block 350, a signal corresponding to the detected ambient noise is inverted for cancellation, and the inverted signal is processed at block 360 with the forward audio leakage transfer function to generate a noise-cancelling signal tailored to an expected amount of ambient noise leaked into the user's ear canal (e.g., past an earbud). At block 380, the noise cancelling signal is added to an input audio signal from an audio source, and presented to a user (as at block 300). The process as shown optionally continues to effect dynamic noise reduction, which may involve sampling of leaked noise and ambient noise with corresponding noise reduction tailored to changing conditions as may relate to earbud movement, changes in ambient conditions and others.

The generation of a noise-cancelling signal at block 360 can be carried out in different manners. For instance, the inversion of the ambient noise signal at block 350 may be omitted, with the ambient noise signal processed first with the forward leakage transfer function to estimate an amount of noise actually entering the user's ear canal. This estimated amount can later be inverted and applied to an audio signal as shown in block 380. In addition, the inversion of the ambient noise signal at block 350 may also be omitted, with the forward transfer function itself being inverted or otherwise modified to generate an inverted signal when processing the detected noise at block 320.

Based upon the above discussion and illustrations, those skilled in the art will readily recognize that various modifications and changes may be made to the present invention without strictly following the exemplary embodiments and applications illustrated and described herein. For example, the forward transfer function can be determined using various characteristics and inputs, such as stored data, predicted data and reflected sound detected using other microphones. The noise cancellation can be carried out using different types of headphones or speaker arrangements, and the control of the application of a cancellation signal can be effected under different control approaches, based upon environmental conditions or otherwise. Such modifications do not depart from the true spirit and scope of the present invention, including that set forth in the following claims.

What is claimed is:

1. An earphone device comprising;

a housing having a proximate end configured for insertion into a user's ear, and a distal end located opposite the proximate end and configured for placement near an outer portion of the user's ear;

a speaker configured and arranged to generate sound based upon an audio signal for passing into the user's ear canal via the proximate end of the housing;

a microphone at the distal end and configured to detect ambient noise and to detect portions of the generated sound leaked from inside the user's ear canal, with the proximate end of the housing inserted into the ear; and a noise reduction circuit configured to generate a forward leakage transfer function for estimating noise entering the user's ear canal, based upon the detected leaked portions of the generated sound, process a signal corresponding to the detected ambient noise with the forward leakage transfer function to generate and output a noise-cancellation signal to cancel at least a portion of the ambient noise that passes into the user's ear canal.

2. The device of claim 1, wherein the noise reduction circuit is configured to generate the forward leakage transfer function by determining a reverse leakage transfer function based on the detected sound leaked out of the ear canal, and generating the forward leakage transfer function based on the reverse leakage transfer function.

3. The device of claim 1, wherein the noise reduction circuit is configured to process the signal corresponding to the detected ambient noise with the forward leakage transfer function to generate a noise-cancellation signal by generating a noise-cancellation signal that, when used to generate audio via a speaker, generates sound corresponding to the inverse of a signal corresponding to ambient noise passing by the proximate end of the housing and entering the user's ear canal.

4. The device of claim 1, wherein the noise reduction circuit is configured to invert the signal corresponding to the detected ambient noise, process a signal corresponding to the detected ambient noise with the forward leakage transfer function to generate a noise-cancellation signal by processing the inverted signal with the forward leakage transfer function to generate the noise-cancellation signal.

5. The device of claim 1, wherein the noise reduction circuit is configured to invert the signal corresponding to the detected ambient noise, process a signal corresponding to the detected ambient noise with the forward leakage transfer function to generate a noise-cancellation signal by multiplying the inverted signal by the forward leakage transfer function to generate the noise-cancellation signal, and output the processed inverted signal for use with the audio signal by adding the noise-cancellation signal to the audio signal.

6. The device of claim 1, wherein the noise reduction circuit is configured to dynamically generate a forward leakage function for adaptively cancelling noise based upon changing characteristics of the forward leakage function relating to the positioning of the housing in a user's ear, and process inverted signals corresponding to noise as varying ambient noise is detected, using a most recent dynamically-generated forward leakage function, and output a varying processed inverted signal for generating variable sound to cancel at least a portion of the ambient noise that passes into the user's ear.

7. The device of claim 1, wherein the noise reduction circuit is configured to receive and use the audio signal to separate a signal from the microphone into a signal corresponding to the generated sound leaked from inside the user's ear canal and a signal corresponding to the ambient noise, for respectively generating a forward leakage transfer function and for generating a noise-cancellation signal.

8. The device of claim 1, wherein the noise reduction circuit is configured to generate a forward leakage transfer function for estimating noise entering the user's ear canal, based upon the detected leaked portions of the generated sound, by generating a reverse leakage transfer function based upon the detected leaked portions of the generated sound, to characterize sound leaking out of the user's ear canal from the proximate end of the housing, and using the reverse leakage transfer function to generate a forward leakage transfer function corresponding to leakage of ambient noise into the user's ear canal.

9. The device of claim 1, wherein the noise reduction circuit is configured to respond to an interruption of the audio signal by using a previously generated forward leakage transfer function to process a signal corresponding to ambient noise detected by the microphone after the audio has been interrupted to generate the noise-cancellation signal, and respond to the audio signal resuming by generating a new forward leakage transfer function using detected portions of sound generated using the resumed audio signal and leaked from inside the ear, and using the new forward leakage transfer function to process a signal corresponding to ambient noise detected by the microphone after the audio signal has resumed to generate the noise-cancellation signal.

10. The device of claim 1, wherein the housing is configured to hold the microphone in a position that is outside the user's ear, with the distal end of the housing being inserted into a portion of the user's ear.

11. The device of claim 1, wherein the earphone device is configured to operate in a configuration mode for filtering select ambient background noise by operating the microphone to detect frequency characteristics of ambient noise to be filtered, and the noise reduction circuit is configured to process a signal corresponding to the detected ambient noise with the forward leakage transfer function by processing a signal corresponding to detected ambient noise in the frequency range of the selected ambient background noise detected by the microphone in the configuration mode, therein reducing noise in the frequency range while facilitating the audibility of ambient sound in other frequency ranges.

12. The device of claim 1, wherein the earphone device is configured to operate in a silent mode by generating the audio signal as a signal that is substantially inaudible to the human ear, using the speaker to generate sound based upon the inaudible signal, using the microphone to detect portions of the generated inaudible sound leaking from the ear canal, in the noise reduction circuit, generate the forward leakage transfer function based upon the detected leaked portions of the generated inaudible sound.

13. The device of claim 1, wherein the earphone device is configured to operate in a white noise mode by generating the audio signal as a signal for generating white noise, using the speaker to generate white noise based upon the generated audio signal, using the microphone to detect portions of the generated white noise leaked from the ear canal, and in the noise reduction circuit, generate the forward leakage transfer function based upon the detected leaked portions of the white noise.

14. An audio noise reduction circuit for reducing ambient noise audible to a user listening to sound generated by an earphone device having a proximate end inserted into the user's ear, a speaker for generating sound in response to an audio signal, and a microphone at a distal end of the earphone device for positioning outside of the user's ear canal, the circuit comprising:

an evaluation circuit configured to determine a forward leakage transfer function for characterizing ambient noise entering the user's ear canal, using a signal corresponding to portions of the generated sound, as detected by the microphone, that has leaked out of the user's ear canal with the proximate end of the earphone inserted in the ear; and a noise reduction circuit configured to process a signal corresponding to ambient noise, detected by the microphone, with the forward leakage transfer function to generate and output a noise-cancelling signal for canceling at least a portion of the detected ambient noise.

15. The circuit of claim 14, wherein the noise reduction circuit is configured to process a signal corresponding to ambient noise detected with the microphone with the forward leakage transfer function to generate and output a noise-cancelling signal by inverting the signal corresponding to ambient noise detected with the microphone, and multiplying the inverted signal by the forward leakage transfer function to generate the noise-cancelling signal.

16. A method for reducing ambient noise audible to a user listening to sound generated by an earphone device having a proximate end inserted into the user's ear, a speaker for generating sound in response to an audio signal, and a microphone at a distal end of the earphone device for positioning outside of the user's ear canal, the method comprising:

in an evaluation circuit, determining a forward leakage transfer function for characterizing ambient noise entering the user's ear canal, using a signal corresponding to portions of the generated sound, as detected by the microphone, that has leaked out of the user's ear canal with the proximate end of the earphone inserted in the ear; and in a noise reduction circuit, processing a signal corresponding to ambient noise, detected by the microphone, with the forward leakage transfer function to generate and output a noise-cancelling signal for canceling at least a portion of the detected ambient noise.

17. The method of claim 16, wherein determining a forward leakage transfer function includes determining a reverse audio leakage transfer function using a signal from the microphone corresponding to detected portions of the generated sound that has leaked out of the user's ear canal with the proximate end of the earphone inserted in the ear, and using the reverse audio leakage function to determine the forward leakage transfer function for characterizing ambient noise entering the user's ear with the proximate end of the earphone inserted therein.

18. The method of claim 16, wherein processing a signal corresponding to ambient noise detected with the microphone with the forward leakage transfer function to generate and output a noise-cancelling signal includes inverting the signal corresponding to ambient noise detected with the microphone, and multiplying the inverted signal by the forward leakage transfer function to generate the noise-cancelling signal.

19. The method of claim 16, wherein determining a forward leakage transfer function includes dynamically generating a forward leakage function for adaptively cancelling noise based upon changing characteristics of the forward leakage function relating to the positioning of the earphone device in the user's ear, and processing a signal corresponding to ambient noise includes processing inverted signals corresponding to noise as varying ambient noise is detected, using a most recent dynamically-generated forward leakage function, and outputting a varying processed inverted signal for generating variable sound to cancel at least a portion of the ambient noise that passes into the user's ear.

20. The device of claim 1, wherein:

the speaker is configured and arranged to generate sound based upon a combination of the audio signal and the noise-cancellation signal; and the noise reduction circuit is configured and arranged to dynamically update the generated forward leakage transfer function during generation of sound based upon a combination of the audio signal and the noise-cancellation signal.

21. The circuit of claim 14, wherein the evaluation circuit is configured to determine the forward leakage transfer function by determining a reverse audio leakage transfer function using a signal from the microphone corresponding to detected portions of the generated sound that has leaked out of the user's ear canal with the proximate end of the earphone inserted in the ear, and using the reverse audio leakage function to determine the forward leakage transfer function for characterizing ambient noise entering the user's ear with the proximate end of the earphone inserted therein.

* * * * *